(12) United States Patent
Farr

(10) Patent No.: US 11,234,597 B1
(45) Date of Patent: Feb. 1, 2022

(54) VIRTUAL STETHOSCOPE AND OTOSCOPE

(71) Applicant: House Calls LLC, Pismo Beach, CA (US)

(72) Inventor: Courtney Farr, Pismo Beach, CA (US)

( * ) Notice: Subject to any disclaimer, the term of this patent is extended or adjusted under 35 U.S.C. 154(b) by 0 days.

(21) Appl. No.: 16/549,601

(22) Filed: Aug. 23, 2019

Related U.S. Application Data

(63) Continuation-in-part of application No. 16/540,623, filed on Aug. 14, 2019, now abandoned.
(Continued)

(51) Int. Cl.
*A61B 5/00* (2006.01)
*A61B 1/00* (2006.01)
(Continued)

(52) U.S. Cl.
CPC ........ *A61B 5/0022* (2013.01); *A61B 1/00016* (2013.01); *A61B 1/042* (2013.01);
(Continued)

(58) Field of Classification Search
CPC ....... A61B 5/00; A61B 5/0002; A61B 5/0015; A61B 5/0022; A61B 7/02; A61B 7/023; A61B 7/026; A61B 7/04; A61B 7/045; A61B 5/0476; A61B 5/048; A61B 5/04845; A61B 5/12; A61B 5/121; A61B 5/123; A61B 5/125; A61B 5/126; A61B 5/128; A61B 1/227; A61B 1/042; A61B 1/00016; A61B 1/00669; A61B 2562/222; A61B 5/6898; A61B 1/0669; G16H 40/20; G16H 40/60; G16H 40/67; G16H 15/00; H04R 1/46; H04R 3/04; H04N 5/2257; H04N 5/2256; H04N 5/38; H04N 2005/2255;
(Continued)

(56) References Cited

U.S. PATENT DOCUMENTS 5,989,186 A * 11/1999 Alatriste ................ A61B 1/227
181/131
2006/0098825 A1* 5/2006 Katz ........................ A61B 7/04
381/67

(Continued)

FOREIGN PATENT DOCUMENTS

GB 1044844 A * 10/1966 ............... A61B 7/04

OTHER PUBLICATIONS

"The Latest on Cellscope's Smartphone-Based Microscope and Otoscope", Jun. 21, 2012, p. 1 (Year: 2012), https://www.medgadget.com/2012/06/the-latest-on-cellscopes-smartphone-based-microscope-and-otoscope.html.*

*Primary Examiner* — Leshui Zhang
(74) *Attorney, Agent, or Firm* — Staniford Tomita LLP

(57) ABSTRACT

The virtual stethoscope and otoscope includes a head having a hollow internal volume with a diaphragm on one side and an otoscope cone on the opposite side. The head is coupled to one end of the tube and a microphone is coupled to an opposite side of the tube. The microphone is coupled to a cable and connector which is attached to a patient computing device. The diaphragm is placed on the patient and the body vibrations produce sound waves which are detected by the microphone. The microphone converts the sound waves into electrical signals which are high/low pass filtered and amplified before being transmitted to the patient computing device which can then transmit the patient data to a medical professional computing device.

18 Claims, 8 Drawing Sheets

Related U.S. Application Data

(60) Provisional application No. 62/748,500, filed on Oct. 21, 2018.

(51) Int. Cl.

| | | |
|---|---|---|
| *A61B 1/04* | (2006.01) | |
| *A61B 1/06* | (2006.01) | |
| *A61B 1/227* | (2006.01) | |
| *A61B 7/04* | (2006.01) | |
| *H04M 1/72409* | (2021.01) | |
| *H04N 5/225* | (2006.01) | |
| *H04N 5/38* | (2006.01) | |
| *H04R 1/46* | (2006.01) | |
| *H04R 3/04* | (2006.01) | |
| *H03F 3/45* | (2006.01) | |

(52) U.S. Cl.
CPC ............ *A61B 1/0669* (2013.01); *A61B 1/227* (2013.01); *A61B 5/6898* (2013.01); *A61B 7/04* (2013.01); *H04M 1/72409* (2021.01); *H04N 5/2256* (2013.01); *H04N 5/2257* (2013.01); *H04N 5/38* (2013.01); *H04R 1/46* (2013.01); *H04R 3/04* (2013.01); *A61B 2562/222* (2013.01); *H03F 3/45071* (2013.01); *H03F 2200/129* (2013.01); *H03F 2203/45116* (2013.01); *H03F 2203/45526* (2013.01); *H04N 2005/2255* (2013.01)

(58) Field of Classification Search
CPC .......... H04M 1/72409; H03F 2200/129; H03F 3/45071; H03F 2203/45526; H03F 2203/45116
USPC .... 381/67, 71.7, 7.11, 7.12, 71.13, 7.14, 72, 381/73.1, 4, 56, 58; 700/94; 600/559; 434/266, 262, 267, 270, 307, 318, 365, 434/396; 327/141, 297; 335/206, 341, 335/20
See application file for complete search history.

(56) References Cited

U.S. PATENT DOCUMENTS

| | | | |
|---|---|---|---|
| 2013/0289353 A1* | 10/2013 | Seth ..................... | A61B 5/0084 600/200 |
| 2014/0180153 A1* | 6/2014 | Zia .......................... | A61B 7/04 600/528 |
| 2015/0087926 A1* | 3/2015 | Raz ........................ | G16H 40/67 600/301 |
| 2018/0168473 A1* | 6/2018 | Du ........................ | A61B 5/6833 |
| 2019/0150756 A1* | 5/2019 | Lee ..................... | A61B 5/0205 |

* cited by examiner

VIRTUAL STETHOSCOPE AND OTOSCOPE

CROSS REFERENCE TO RELATED PATENT APPLICATIONS

This patent application is a continuation-in-part of U.S. patent application Ser. No. 16/540,623, "Virtual Stethoscope And Otoscope" filed Aug. 14, 2019, which claims priority to U.S. Provisional Patent Application No. 62/748,500, "Virtual Stethoscope And Otoscope With Microphone" filed Oct. 21, 2018 which is hereby incorporated by reference in its entirety.

BACKGROUND

Virtual medical care is becoming mainstream in the healthcare world. Many doctor's offices, insurance companies, hospitals and healthcare organizations are integrating virtual medical care into their practice. The problem is that the movement toward virtual medical care is moving faster than the advancement of tools that we use to diagnose and treat our patients. An adequate medical diagnosis can be made using approximately 62% patient history (interview), 17% physical exam findings, and 20% diagnostic tests. What is needed is a system that allows for complete diagnosis made by a remotely located medical professional with a virtual diagnostic stethoscope and/or otoscope.

SUMMARY OF THE INVENTION

The inventive virtual stethoscope/otoscope includes a head with a diaphragm on one side and an otoscope cone on the opposite side. In this application the term "virtual" is intended to mean a real stethoscope/otoscope mechanism which can produce data which is transmitted to a remotely located medical professional. The head is coupled to one end of a hollow tube and a microphone is coupled to the opposite end of the tube. The microphone is coupled to a cable and connector which is attached to a patient computing device.

In an embodiment, the diaphragm is made of a transparent material so that external light can travel through the diaphragm to illuminate the patient through an orifice at the end of the otoscope cone. In addition or alternatively, a light source can be integrated with the virtual otoscope which can direct light through the orifice at the end of the otoscope cone orifice. A camera can be placed on the outer surface of the diaphragm facing the otoscope cone. The camera can be built into a mobile computing device such as a smartphone or tablet. The camera can take optical images of the patient through the orifice at the tip of the otoscope cone.

In another embodiment, the virtual stethoscope/otoscope can have an integrated camera and light source. The light can be turned on to illuminate the patient through the orifice at the tip of the otoscope cone. The reflected light can be captured by the camera. The optical data can be transmitted to the patient computing device.

In the stethoscope mode, the diaphragm is placed on the patient and the body vibrations produce sound waves in the hollow tube which are detected by the microphone. The microphone converts the sound waves into electrical signals which are amplified by the patient computing device. The electrical signals can be transmitted to a medical professional computing device, allowing the medical professional to listen to the patient. The medical professional can communicate with the patient via text messaging, video chat, or other computer to computer communications means.

In the otoscope mode, the otoscope cone can be positioned to view a portion of the patient such as the inner ear. A camera which can be in the patient computing device can convert the photo data into electrical signals which are received by a software application program running on the patient computing device and transmitted to the medical professional computing device. The medical professional can view the patient remotely and provide feedback through text messaging, video chat, or other computer to computer communications means.

If the otoscope has an integrated camera, the camera can receive optical images and transmit these images to the software application program running on the patient computing device and transmitted to the medical professional computing device. The medical professional can view the patient remotely and provide feedback through text messaging, video chat, or other computer to computer communications means.

DETAILED DESCRIPTION

Figure 1:
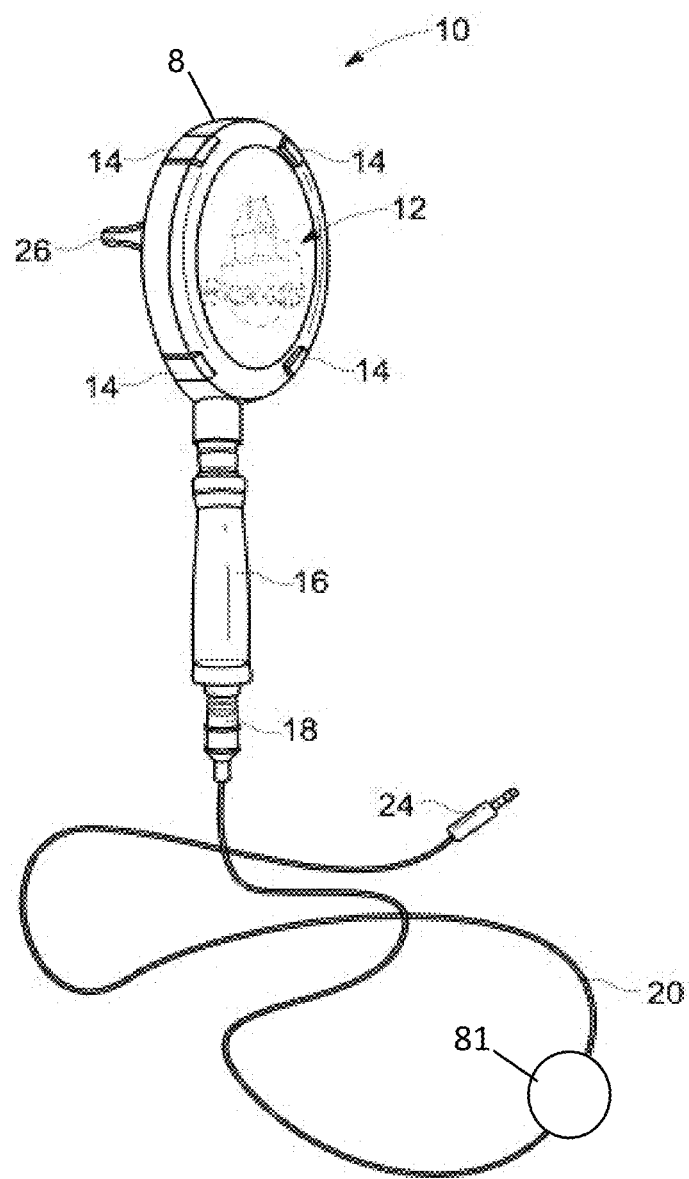
FIG. 1 illustrates a perspective side view of an embodiment of a virtual stethoscope/otoscope.

FIG. 1 is a perspective view of an embodiment of a virtual stethoscope/otoscope 10. An upper portion of the stethoscope/otoscope 10 has brackets 14 mounted to head 8 of the virtual stethoscope 10 which secure the diaphragm 12 to the front of the stethoscope 10. In this embodiment there are four brackets 14 mounted around the perimeter of the head 8. The virtual stethoscope head 8 is connected to a first end of a hollow stethoscope tube 16. In the illustrated embodiment, the back of the virtual stethoscope head 8 has an otoscope head tip 26. In an embodiment, the diaphragm 12 can be made of translucent plastic that allows transmission of light from an external light source. The filtered light is then transmitted through the hole at the tip of the otoscope head tip 26.

A second end of the tube 16 is connected to a microphone 18. The microphone 18 is connected to a microphone cord 20 which is coupled at the far end to a microphone plug 24. In an embodiment, an amplifier and filter unit 81 can be coupled to the microphone cord 20 which can amplify and filter the electrical signals from the microphone 18.

Figure 2:
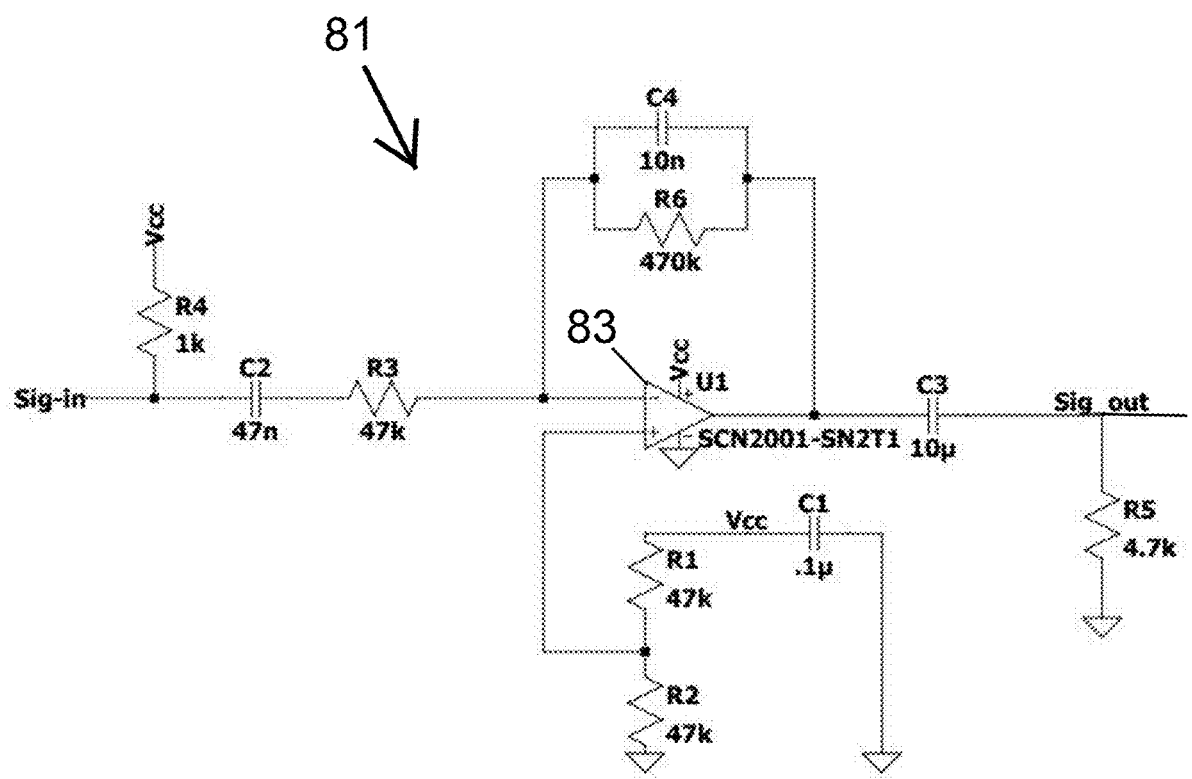
FIG. 2 illustrates a schematic diagram of an amplifier and filter circuit.

FIG. 2 illustrates a schematic of an application and filter unit 81. For example, the amplifier and filter unit 81 can amplify the electrical signal by 20 decibels (dB) and provide a low pass filter which filters and removes electrical frequencies under a selected low cutoff frequency and a high pass filter which filters and removes electrical frequencies over a selected high cutoff frequency. The cutoff frequency value for the low pass and the high pass filters are not absolute. At frequencies below the selected low cutoff frequency the transmitted electrical signals start to decrease gradually. Similarly, for the high pass filter, frequencies above the selected high cutoff frequency also decrease gradually.

In an embodiment, the selected low cutoff frequency and the selected high cutoff frequency are both below 100 Hz. In a more specific embodiment, the high cutoff frequency is between 55 hertz (Hz) and 100 Hz and the low cutoff frequency is between 20 Hz and 55 Hz. In the illustrated embodiment shown in FIG. 2, the selected low cutoff frequency can be 33.8 hertz (Hz) and the selected high cutoff frequency can be 72 Hz. Thus, the electrical signals having frequencies that are smaller than 72 Hz and those larger than 33.8 Hz are still getting through the filter unit 81. By choosing such cutoff values, a very limited range of sound frequencies can pass through the low pass and high pass filters of the circuit 81. The circuit 81 filters out almost all unwanted sounds such as static noise caused by contact between diaphragm and skin. However, because a large portion of the electrical signal can be filtered and removed, the magnitude of the signal can be significantly reduced. The amplifier 83 can amplify the electrical signal "Sig-in" by factor of 10 to compensate for the signal loss due to the low pass and high pass filters.

In the illustrated example, the amplifier 83 can be a model NCS2001-SN2T1 which is available from ON Semiconductor. The Vcc applied to the amplifier 83 can be 3.7 Volts direct current (Vdc) which can amplify the electrical signal by a factor of 10 or by an amplifier gain of 20 decibels (dB). Table 1 below lists the specific values of the resisters and capacitors illustrated in FIG. 2.

TABLE 1

| Label | Component Description |
|---|---|
| R1, R2, R3, R4, R5, R6 | 47 k ohm, 47 k ohm, 47 k ohm, 1 k ohm, 4.7 k ohm, 4.7 k ohm |
| C1, C2, C3, C4 | 1 μ Farad (F), 47 nF, 10 μF, 10 nF |
| U1 | NCS2001-SN2T1 |
| Vcc | 3.7 volts direct current |

Figure 3:
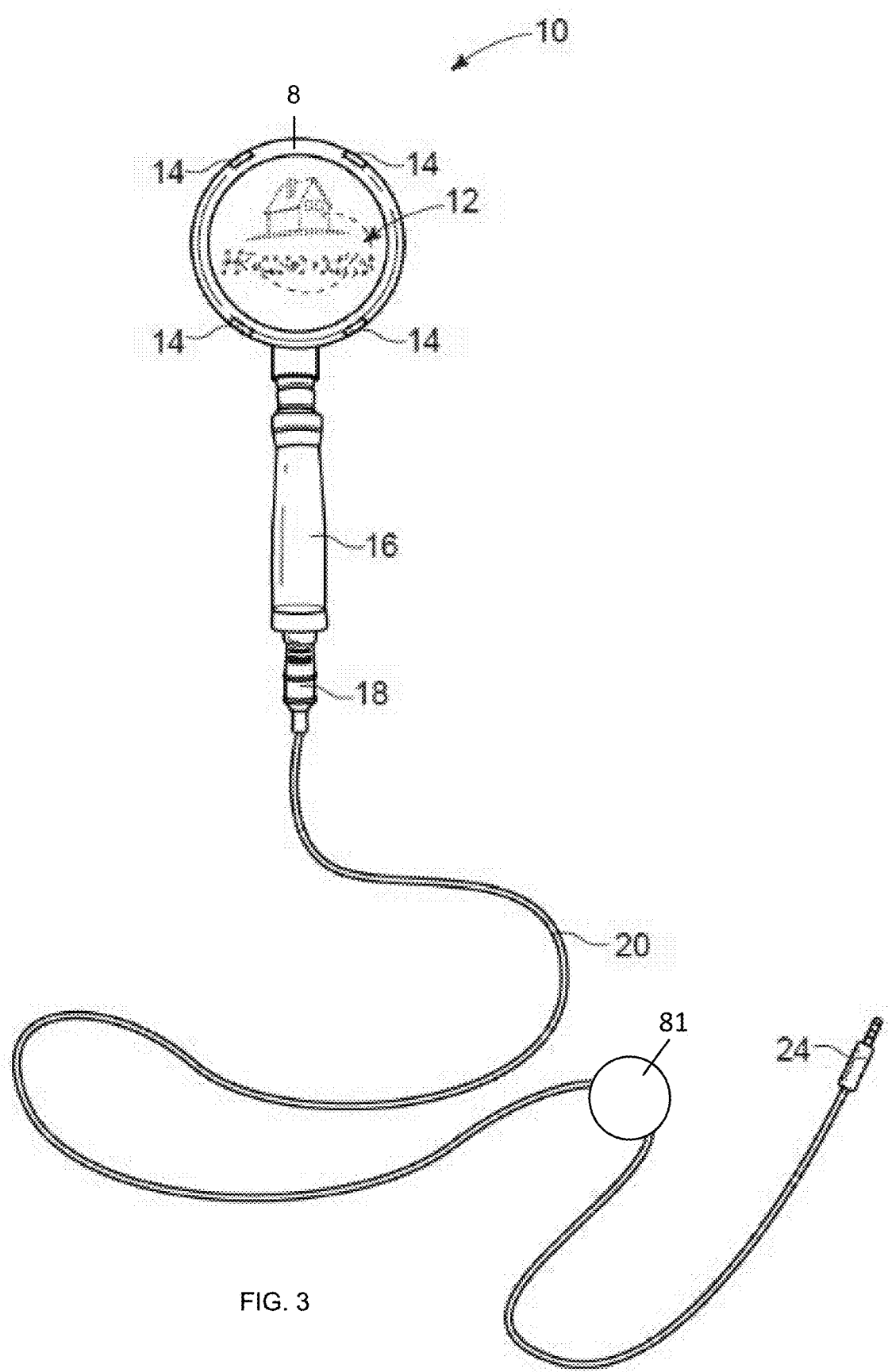
FIG. 3 illustrates a front view of an embodiment of a virtual stethoscope.

FIG. 3 is a front view of the virtual stethoscope 10 showing the diaphragm 12 which is circular in shape and attached to the head 8. The diaphragm 12 is attached to the front of the stethoscope 10 with a plurality of brackets 14. In this example, the brackets 14 are at the upper left, upper right, lower left, and lower right portions of the head 8 of the virtual stethoscope 10. The virtual stethoscope head 10 is connected to the upper end of the hollow stethoscope tube 16. The microphone 18 is connected to the lower end of the tube 16. The microphone 18 is a transducer which converts sound waves into electrical signals. The microphone 18 is connected to the microphone cord 20 and amplifier and filter unit 81. A microphone plug 24 is attached to the end of the microphone cord 20.

Figure 4:
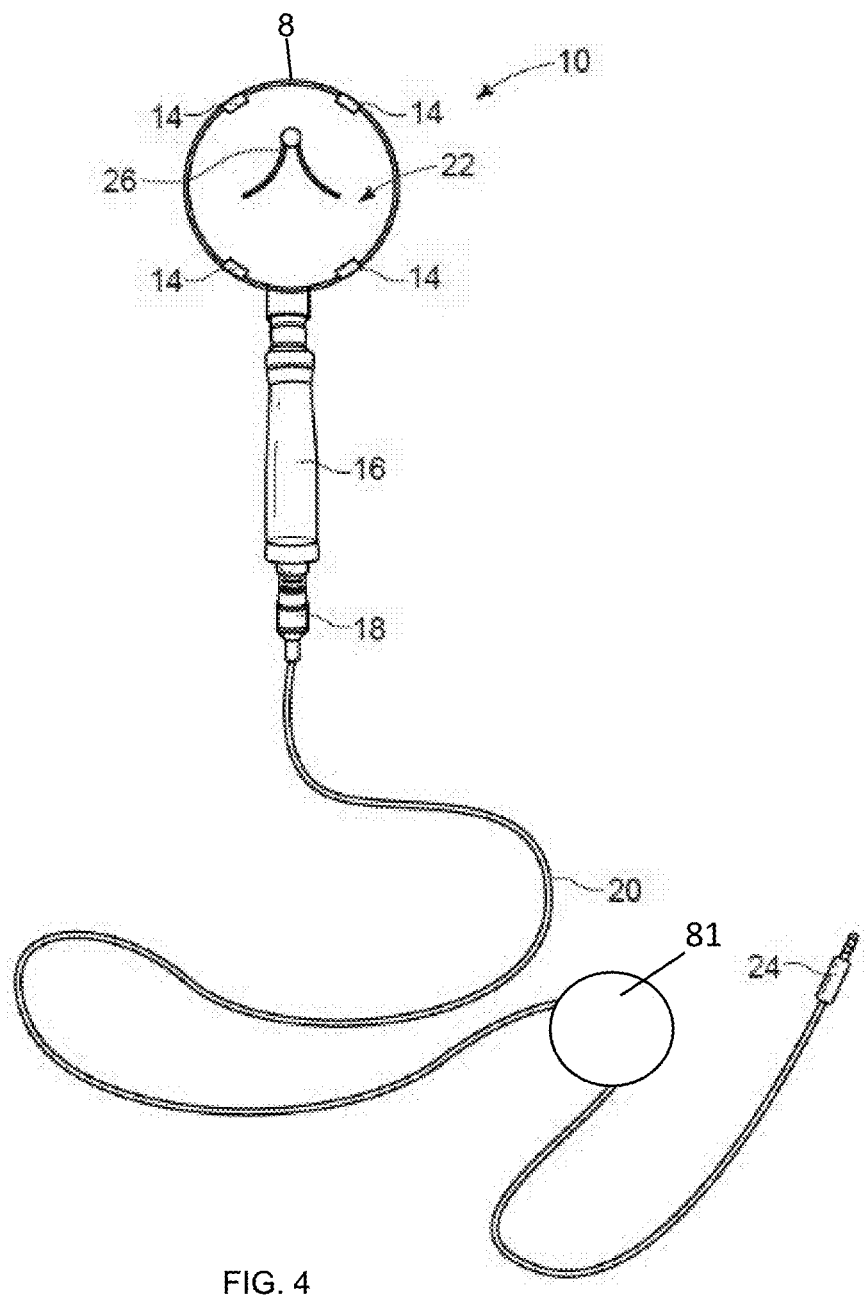
FIG. 4 illustrates a rear view of an embodiment of a virtual stethoscope.

FIG. 4 is a back view of the virtual stethoscope 10 showing the otoscope head 22 and an orifice at the tip 26 which is attached to the back of the head 8 with brackets 14. The conical otoscope head 22 is hollow and has a hole at the tip end 26 which transmits light from an internal or external light source.

Figure 5:
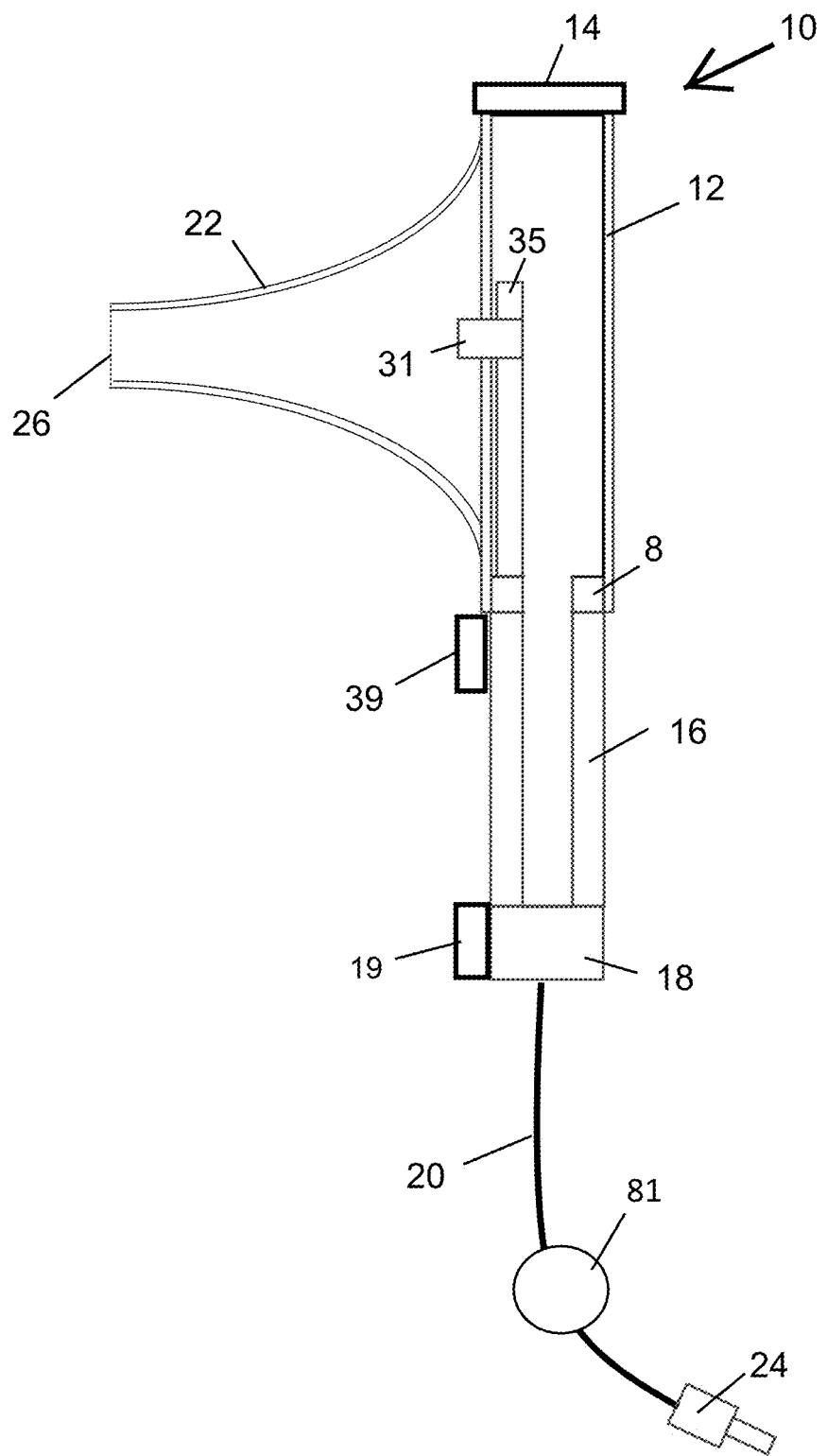
FIG. 5 illustrates a cross section side view of an embodiment of a virtual stethoscope with an internal camera.

FIG. 5 illustrates a cross section view of the virtual stethoscope 10. The head 8 has a hollow internal volume with a diaphragm 12 on one side and a conical otoscope head 22 with an orifice tip 26 on the opposite side. A camera 31 and an internal light source 35 can be mounted in the internal hollow volume of the head 8. The camera 31 and the light source 35 can be coupled to a switch 39 which allows a user to actuate the switch 39 to turn on the camera 31 and/or internal light source 35. The camera 31 and the internal light source 35 can be directed towards the center orifice tip 26.

For the camera 31 to detect optical images through the orifice tip 26, a light source is needed. An external light source can transmit light through the diaphragm 12 into the internal volume of the head 8 and through the tip 26 to objects adjacent to the tip 26. When the external light is insufficient, the internal light source 35 can be used. When turned on, the light source 35 directs visible light through the center orifice of the conical otoscope head tip 26. In an embodiment, the light source 35 can be a light emitting diode (LED) which receives electrical power through the electrical conductor cord 20 and emits visible light. The light source 35 can be offset from the camera 31 so light does not travel directly from the light source 35 to the camera 31 sensor surface.

When the camera 31 is turned on and starts to record, the camera 31 will detect the optical images through the orifice in the otoscope head tip 26 and output electrical signals representing the detected optical images. The camera 31 can also receive electrical power through the electrical conductor cord 20 and transmit photograph and/or video signals through the electrical conductor cord 20 and connector 24 to an external computing device.

The hollow tube 16 is mounted to the head 8 with the center hole of the hollow tube 16 connected to the volume of the head 8. When the diaphragm 12 vibrates, the sound waves travel from the head 8 through the hollow tube 16 to the microphone 18. The microphone 18 converts the sound waves into electrical signals which are transmitted through the electrical cord 20 which can be coupled to an external computing device.

In use, the inventive virtual stethoscope can provide the same function as a normal stethoscope. The diaphragm 12 of the stethoscope 10 is held against a portion of the human body, normally the chest or over a blood vessel. The movements of the body due to body functions such as heart beat, sneezing, breathing, or coughing cause the diaphragm 12 to vibrate. These body sound waves are transmitted from the diaphragm 12 through the hollow stethoscope tube 16 to the microphone 18 which converts the sound waves into electrical signals. The microphone 18 emits electrical signals representing the detected sound through the microphone cord 20, amplifier and filter unit 81, and microphone plug 24. The plug 24 can be coupled to a computing device such as a smart phone or a computer that can transmit the electrical signals from the microphone 18 to a remote computing device, smart phone or other listening device which can output an audio signal which can be heard by a medical professional such as a clinician, nurse, and/or doctor.

In other embodiments, the stethoscope 10 can include a wireless transmitter 19 which can convert the image data and audio data into radio frequency signals which are transmitted to the patient computing device and then to the remote medical professional computer. The inventive system allows the remote medical professionals to hear the normal stethoscope sounds as captured by the microphone 18 and possibly diagnose medical issues that are detected based upon the stethoscope output.

Figure 6:
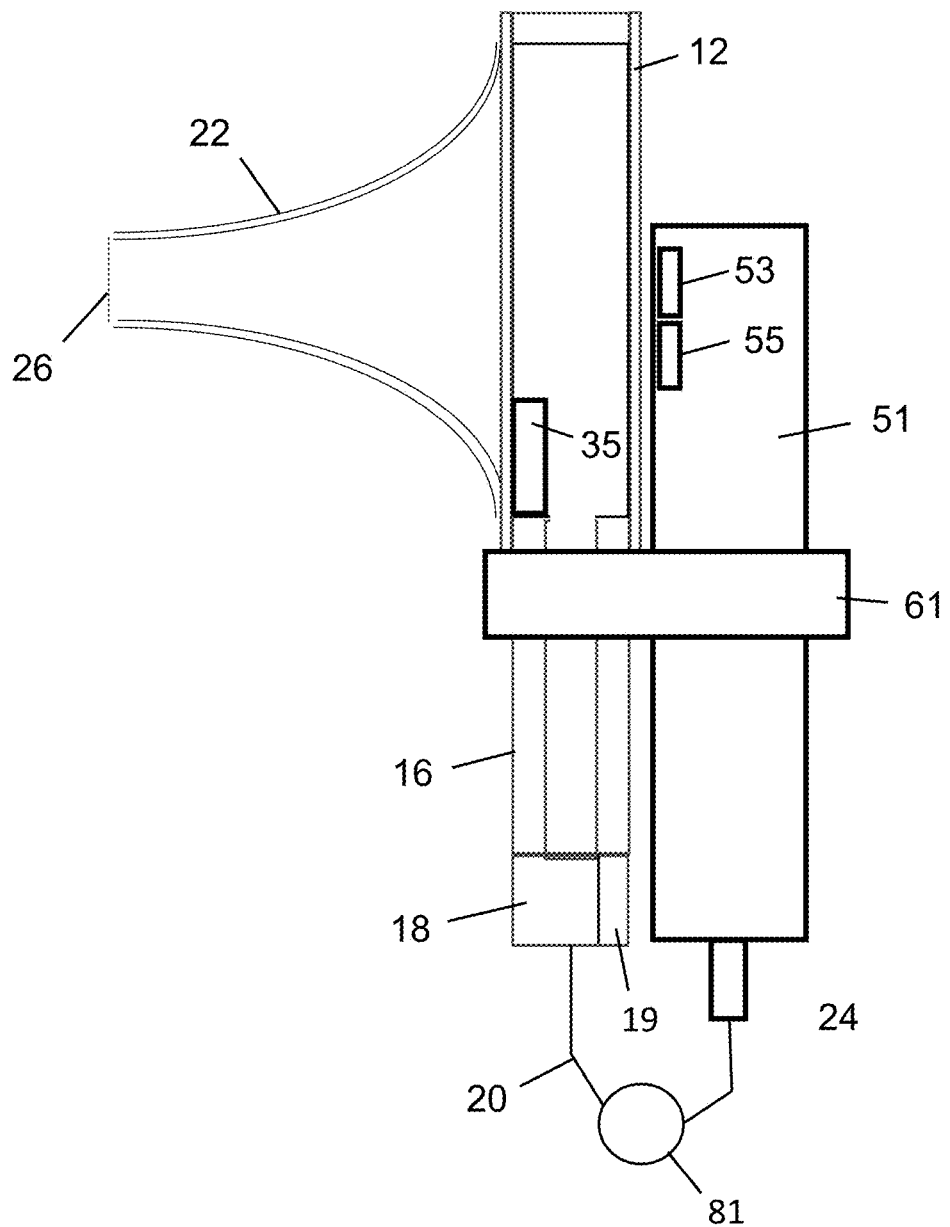
FIG. 6 illustrates a cross section side view of an embodiment of a virtual stethoscope.

FIG. 6 illustrates the virtual stethoscope 10 attached to an external device 51 which can include a camera 53 and a light source 55 with a brace 61 or other coupling mechanism. The external device 51 can be a computing device such as a smart phone or tablet and can include an external light source 55 and external video camera 53. In this embodiment, the diaphragm 12 can be constructed of a transparent or translucent material such as transparent plastic or alternatively, the diaphragm 12 can be removed. A clear or removed diaphragm 12 allows external light from the external light source 55 or ambient light to pass through the virtual stethoscope head 10 into the otoscope head tip 26. Objects on the opposite side of the head tip 26 are illuminated and reflected light will pass back through the otoscope head tip 26 and the diaphragm 12 to the camera 53. The illuminated visual images can be captured and recorded by the camera 53 in the external device 51. The external device 51 can convert the visual images into electrical signals which can be transmitted to a remote computing device which can be coupled to a remote visual display.

In an embodiment, the stethoscope 10 can have an integrated light source 35. The internal light source 35 can emit visual light through the otoscope head tip 26. Objects on the opposite side of the head tip 26 are illuminated and reflected light will pass back through the otoscope head tip 26 and the diaphragm 12 to the camera 53. The illuminated visual images can be captured and recorded by the camera 53 in the external device 51 which can be a mobile computing device such as a smart phone or a tablet computer. Similarly, the audio stethoscope data can be captured and recorded by the external device 51 through the cable 20, amplifier and filter unit 81, and connector 24. The external device 51 can convert the visual images (and audio signals) into video signals which can be displayed on the external device 51. The image and audio data can also be transmitted from the external device 51 to a remote computing device which can be coupled to a remote visual display which can be seen by a remotely located medical professional.

In other embodiments, the stethoscope 10 can include a wireless transmitter 19 which can convert the image data and audio data into radio frequency signals which are transmitted to the patient computing device and then to the remote medical professional computer. The inventive system allows the remote medical professionals to hear the normal stethoscope sounds as captured by the microphone 18 and possibly diagnose medical issues that are detected based upon the stethoscope output.

Figure 7:
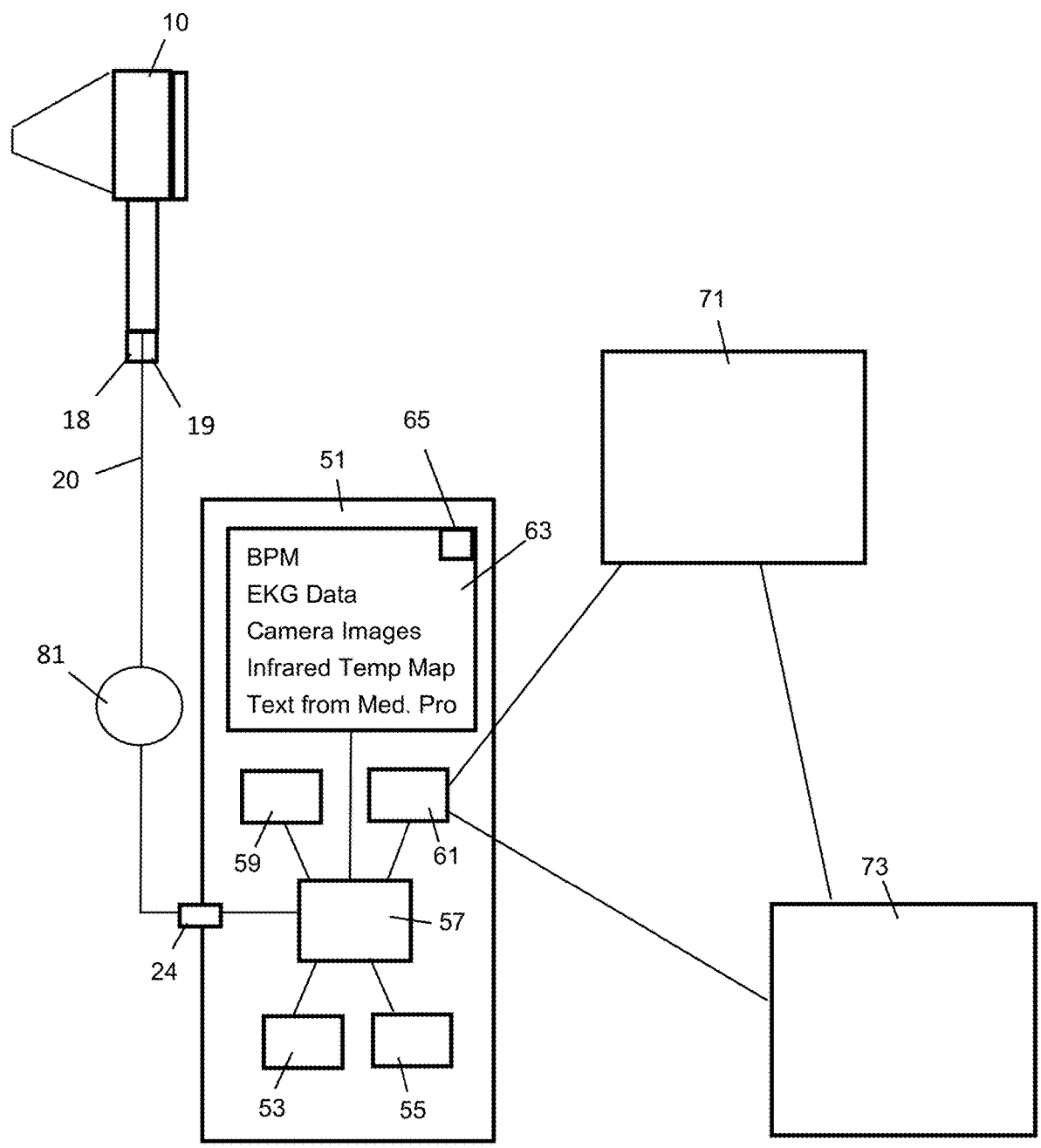
FIG. 7 illustrates a block diagram of the virtual stethoscope and patient computing device used with a computer network.

With reference to FIG. 7, a block diagram is illustrated which shows the stethoscope/otoscope 10 coupled to a computing device 51. When the internal camera is used, image data and stethoscope audio data can be transmitted from the camera 53 through the cable 20 to the plug 24 coupled to a computing device 51 which can be a smart phone, tablet, laptop computer, or other computing device. The computing device 51 can include a processor 57 running software which can be a downloadable mobile application (app). The image data and stethoscope audio data can be received by a processor 57 which can process this data as controlled by the mobile app. In other embodiments, the camera 53 and light source 55 from the computing device 51 can be used to obtain patient data. The image data can be transmitted from the camera 53 to the processor 57 and the audio data can be transmitted from the microphone 18 through the cable cord 20 and amplifier and filter unit 81 to the plug 24 coupled to the processor 57. The stethoscope 10 can include a wireless transmitter 19 which can convert the image data and audio data into radio frequency signals which are transmitted to a transceiver 61 which can forward the data to the processor 57. The processor 57 can amplify the sound from the stethoscope and enhance and/or filter the video signals from the camera 53.

The computing device 51 can include input/output (I/O) devices coupled to the processor 57 such as a touch screen 63 and audio output 65 such as speaker or headphones. The mobile app can be downloaded and stored in the memory 59 and run by the processor 57. When the processor 57 runs the mobile app, the system can provide a graphical user interface (GUI) which can display patient data and operating controls on the touch screen 63. The user can input mobile app controls through the GUI so that the computing device 51 displays data on a touch screen 63 such as heart rate in beats per minute (BPM), EKG data, Camera images, infrared temperature map from infrared camera images, and text data from a medical professional from a remote computer.

The image camera data and the audio stethoscope data can be captured and recorded by the external device 51 and stored in memory 59. The visual images and audio signals can also be displayed on the touch screen 63. The image and audio data can be transmitted by a transceiver 61 from the external device 51 to a remote medical professional computing device 73 which can be coupled to a remote visual display which can be seen by a remotely located medical professional. The medical professional can review the patient data and provide feedback which can be transmitted and output by the external device 51 as audio or visual data on the touch screen 63.

In other embodiments, the system components can be part of a large network of patient and medical professional computing devices which are all in communication with cloud based server 71. In this embodiment, the image and audio data can also be transmitted by a transceiver 61 from the external device 51 to a cloud server 71 which can store the data in a Health Insurance Portability and Accountability Act (HIPAA) compliant manner. The cloud server 71 can then transmit the image and audio data from the external device 51 to a remote medical professional computing device 73. The medical professional can review the patient data and provide feedback which can be transmitted back through the cloud server 71 to the external device 51 as audio or visual data on the touch screen 63.

In actual use, the patient schedules an appointment with a medical professional. At the scheduled appointment time, the patient and medical professional can implement video chat communications with a computing device such as a smart phone, tablet, or computer. During the video chat, the patient can plug the virtual stethoscope/otoscope into the patient computing device. The audio and video signals are transmitted from the virtual stethoscope/otoscope to the patient computing device to a medical professional computing device in real time. The medical professional can then perform a virtual examination which can include listening to heart/lungs and/or looking into ear of the patient. Through the video chat, the patient can be instructed on how to use the virtual stethoscope/otoscope. For example, the instructions can include placement and adjustments to the virtual stethoscope/otoscope. In addition to transmitting the audio and video signals to the medical professional computing device, this information can also be displayed on the patient's computing device which can be heard and seen by the patient. Based upon the transmitted information, the medical professional can provide medical advice and treatments to the patient. If there are conditions that need closer examination, the medical professional may schedule an in person meeting.

The otoscope can be used for various medical purposes. The otoscope head can be placed into a human ear as is the normal manner for visualization of the inner ear. The medical professional can visually identify redness, inflammation, infection, ear wax, etc. Based upon the appearance of the inner ear, the medical professional may be able to suggest medicine or medical procedures for resolving ailments of the patient. Some of the possible alternative uses include: rectal exams, vaginal exams, fetal heart beat detection, and doppler ultrasound exams for limbs. In an embodiment, the otoscope head can be replaced with an ophthalmoscope attachment which can be used to convert the otoscope into an ophthalmoscope.

By enabling remote access to patients this device can increase access to care worldwide, enabling medical diagnosis and treatment by remotely located medical professionals. This can allow patients to gain access to medical care in areas where medical services may not be available, including remote, dangerous, and disaster relief regions. This virtual stethoscope/otoscope would additionally bring specialty and urgent care to remote areas as well as provide remote monitoring of chronic diseases and acute diagnoses to patients. As long as there is cell phone, satellite or computer internet access, the virtual stethoscope can be used for live video conferencing and treatment anywhere.

Figure 8:
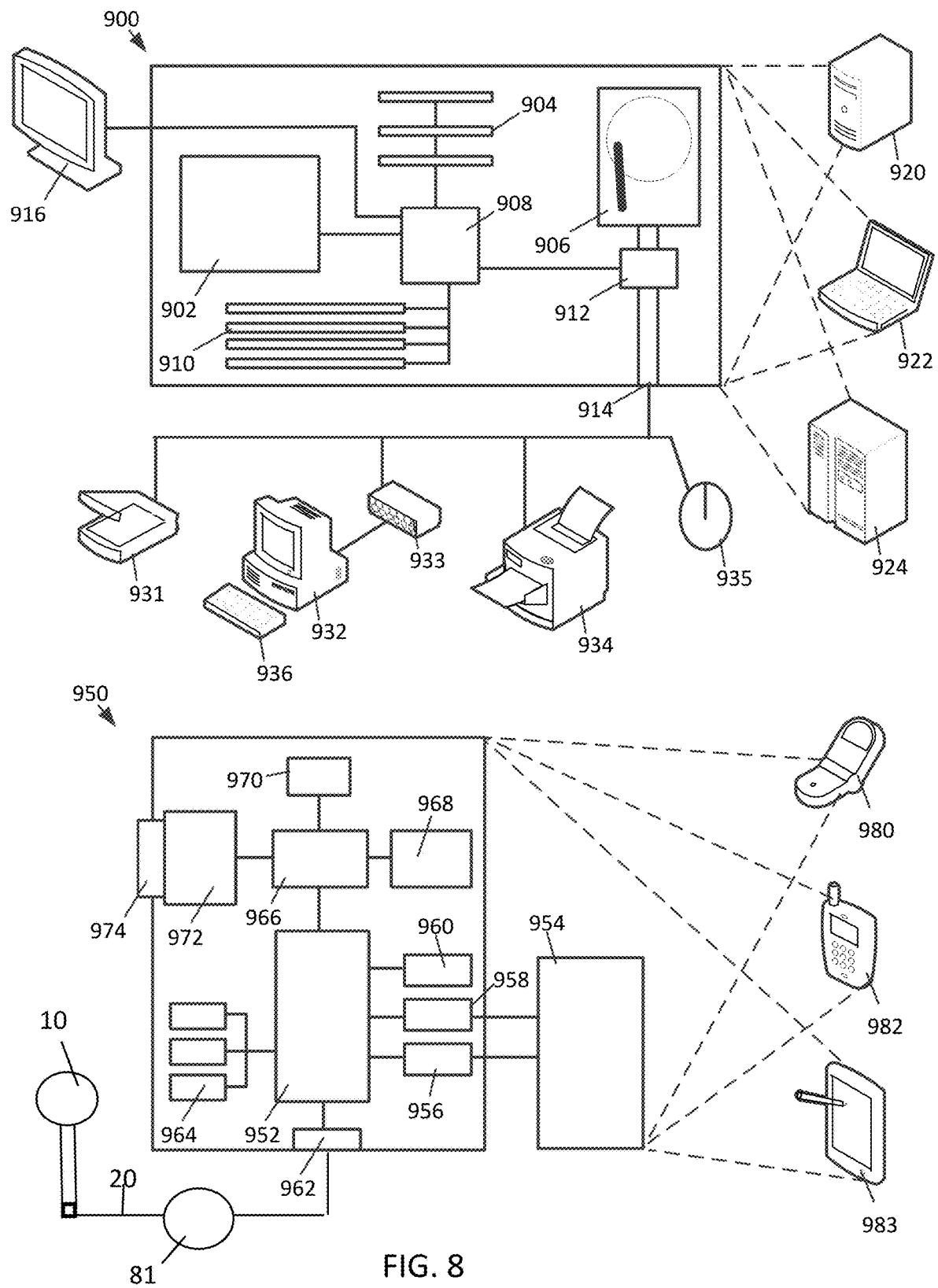
FIG. 8 illustrates a generic computer system.

FIG. 8 shows an example of a generic computer device 900 and a generic mobile computer device 950, which may be used to implement the processes described herein, including the mobile-side and server-side processes for installing a computer program from a mobile device to a computer. Computing device 900 is intended to represent various forms of digital computers, such as laptops, desktops, workstations, personal digital assistants, servers, blade servers, mainframes, and other appropriate computers. Computing device 950 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 900 includes a processor 902, memory 904, a high-speed interface 908 connecting to memory 904 and high-speed expansion ports 910, and a low speed interface 912 connecting to low speed bus 914 and storage device 906. Each of the components processor 902, memory 904, storage device 906, high-speed interface 908, high-speed expansion ports 910, and low speed interface 912 are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external I/O device, such as display 916 coupled to high speed interface 908. In other implementations, multiple processors and/or multiple busses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier may be a non-transitory computer- or machine-readable storage medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port 914, which may include various communication ports (e.g., USB, Bluetooth, Ethernet, wireless Ethernet), may be coupled to one or more I/O devices, such as a keyboard 936 in communication with a computer 932, a pointing device 935, a scanner 931, or a networking device 933 such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an I/O device such as a display 954, a communication interface 966, and a transceiver 968, among other components. The device 950 may also be provided with a storage device, such as a Microdrive, solid state memory or other device, to provide additional storage. Each of the components computing device 950, processor 952, memory 964, display 954, communication interface 966, and transceiver 968 are interconnected using various busses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a Thin-Film-Transistor Liquid Crystal Display (TFT LCD) or an Organic Light Emitting Diode (OLED) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provided in communication with processor 952, so as to enable near area communication of device 950 with other devices. External interface 962 may provide, for example, for wired communication in some implementations, or for wireless communication in other implementations, and multiple interfaces may also be used. In this example, the described stethoscope/otoscope 10 is coupled to a cable 20 and an amplifier and filter unit 81 which can be coupled to the computing device 950 through the external interface 962. In other embodiments, the stethoscope/otoscope 10 can communicate with the device 950 with a wireless transmitter 19 and receiver module 970.

The memory 964 stores information within the computing device 950. The memory 964 can be implemented as one or more of a computer-readable medium or media, a volatile memory unit or units, or a non-volatile memory unit or units. Expansion memory 974 may also be provided and connected to device 950 through expansion interface 972, which may include, for example, a Single In Line Memory Module (SIMM) card interface. Such expansion memory 974 may provide extra storage space for device 950 or may also store applications or other information for device 950. Specifically, expansion memory 974 may include instructions to carry out or supplement the processes described above and may include secure information also. Thus, for example, expansion memory 974 may be provide as a security module for device 950 and may be programmed with instructions that permit secure use of device 950. In addition, secure applications may be provided via the SIMM cards, along with additional information, such as placing identifying information on the SIMM card in a non-hackable manner.

The memory may include, for example, flash memory and/or Non-Volatile Random Access Memory (NVRAM), as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 974, memory on processor 952, or a propagated signal that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, Wi-Fi, or other such transceiver (not shown). In addition, GPS (Global Positioning System) receiver module 970 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smartphone 982, personal digital assistant, a tablet computer 983 or other similar mobile computing device.

Various implementations of the systems and techniques described here can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

The present disclosure, in various embodiments, includes components, methods, processes, systems, and/or apparatus substantially as depicted and described herein, including various embodiments, sub-combinations, and subsets thereof. Those of skill in the art will understand how to make and use the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease, and/or reducing cost of implementation. Rather, as the following claims reflect, inventive aspects lie in less than all features of any single foregoing disclosed embodiment.

What is claimed is:

1. A medical apparatus comprising:
an otoscope cone having a hole at a tip of the otoscope cone;
a head having a perimeter structure surrounding a hollow internal volume and a translucent stethoscope diaphragm attached to a stethoscope side of the hollow internal volume of the head and the otoscope cone is coupled to an otoscope side of the hollow internal volume of the head that is opposite the stethoscope side of the head, wherein the translucent stethoscope diaphragm and the stethoscope side of the head are opposite the otoscope cone coupled and the otoscope side of the head and define side surfaces of the hollow internal volume;
a first end of a tube coupled to a side surface of the head;
a microphone coupled to a second end of the tube for converting sound vibrations from the translucent stethoscope diaphragm into electrical signals;
an amplifier and filter unit having a filter for processing the electrical signals from the microphone by removing the electrical signals having frequencies above a high cutoff frequency and below a low cutoff frequency and an amplifier for amplifying the electrical signals that are between the high cutoff frequency and below the low cutoff frequency;
a first portion of a microphone cord between the microphone and the amplifier and filter unit; and
a second portion of the microphone cord between the amplifier and filter unit and a connector that is coupled to a computing device.

2. The medical apparatus of claim 1 wherein the high cutoff frequency and the low cutoff frequency are below 100 hertz (Hz).

3. The medical apparatus of claim 1 wherein the high cutoff frequency is between 55 hertz (Hz) and 100 Hz and the low cutoff frequency is between 20 Hz and 55 Hz.

4. The medical apparatus of claim 1 wherein the high cutoff frequency is 72 hertz (Hz) and the low cutoff frequency is 33.8 Hz.

5. The medical apparatus of claim 1 further comprising:
a radio frequency transmitter coupled to an electrical outlet of the amplifier.

6. The medical apparatus of claim 1 further comprising:
a radio frequency transmitter coupled to an electrical outlet of the amplifier; and
a smart phone having a radio frequency receiver, wherein the smart phone receives radio frequency signals from the radio frequency transmitter and transmits signals from the microphone to a remote computing device.

7. The medical apparatus of claim 1 further comprising:
a radio frequency transmitter coupled to an electrical outlet of the amplifier; and
a smart phone having a radio frequency receiver, wherein the smart phone displays information derived from the microphone.

8. The medical apparatus of claim 1 further comprising:
a camera in the head directed towards the hole at the tip of the otoscope cone.

9. The medical apparatus of claim 1 further comprising:
a light source in the head directed towards the hole at tip of the otoscope cone; and
a camera placed against the translucent stethoscope diaphragm and directed towards the hole at the tip of the otoscope cone.

10. The medical apparatus of claim 1 further comprising:
a light source in the head directed towards the hole at the tip of the otoscope cone; and
a dimmer coupled to the light source for controlling the light output from the light source.

11. The medical apparatus of claim 1 further comprising:
a camera in the head directed towards the hole at the tip of the otoscope cone wherein an electrical cable is coupled to an electrical outlet of the camera.

12. The medical apparatus of claim 1 further comprising:
a camera in the head directed towards the hole at the tip of the otoscope cone wherein an electrical cable is coupled to an electrical outlet of the camera; and
a smart phone connected to an electrical connector coupled to the electrical cable wherein the smart phone transmits electrical signals from the camera to the computing device.

13. The medical apparatus of claim 1 further comprising:
a camera in the head directed towards the hole at the tip of the otoscope cone; and
a radio frequency transmitter coupled to the electrical outlet of the camera.

14. The medical apparatus of claim 1 further comprising:
a camera in the head directed towards the hole at the tip of the otoscope cone;
a radio frequency transmitter coupled to an electrical outlet of the camera; and
a smart phone having a radio frequency receiver, wherein the smart phone receives radio frequency signals from the radio frequency transmitter and transmits signals from the camera to a remote computing device.

15. The medical apparatus of claim 1 further comprising:
a camera in the head directed towards the hole at the tip of the otoscope cone;
a radio frequency transmitter coupled to an electrical outlet of the camera; and
a smart phone having a radio frequency receiver, wherein the smart phone displays information derived from the camera.

16. A medical apparatus comprising:
a head having a perimeter structure surrounding a hollow internal volume;
an otoscope cone coupled to an otoscope side of the hollow internal volume of the head, the otoscope cone having a hole at a tip of the otoscope cone;

a translucent stethoscope diaphragm attached to a stethoscope side of the hollow internal volume of the head that is opposite the otoscope side of the head;

a microphone coupled to the hollow internal volume for converting sound vibrations from the translucent stethoscope diaphragm into electrical signals, wherein the translucent stethoscope diaphragm and the stethoscope side of the head are opposite the otoscope cone coupled and the otoscope side of the head and define side surfaces of the hollow internal volume;

an amplifier and filter unit having a filter for removing electrical signals having frequencies above a high cutoff frequency and below a low cutoff frequency and an amplifier for amplifying the electrical signals that are between the high cutoff frequency and below the low cutoff frequency;

a first portion of a microphone cord between the microphone and the amplifier and filter unit; and a second portion of the microphone cord between the amplifier and filter unit and a connector that is coupled to a computing device.

17. The medical apparatus of claim 16 wherein the high cutoff frequency is between 55 hertz (Hz) and 100 Hz and the low cutoff frequency is between 20 Hz and 55 Hz.

18. The medical apparatus of claim 16 further comprising:

an electrical cable coupled to an electrical outlet of the amplifier;

an electrical connector coupled to the electrical cable; and a smart phone connected to the electrical connector coupled to the electrical cable wherein the smart phone transmits the electrical signals from the microphone to a remote computing device.

* * * * *